United States Patent [19]

Miyashita et al.

[11] Patent Number: 5,508,800
[45] Date of Patent: Apr. 16, 1996

[54] SEMICONDUCTOR SUBSTRATE, METHOD OF MANUFACTURING SEMICONDUCTOR SUBSTRATE AND SEMICONDUCTOR DEVICE, AND METHOD OF INSPECTING AND EVALUATING SEMICONDUCTOR SUBSTRATE

[75] Inventors: Moriya Miyashita; Hachiro Hiratsuka; Atsuko Kubota; Shuichi Samata; Masanori Numano; Hiroyuki Fukui, all of Yokohama, Japan

[73] Assignee: Kabushiki Kaisha Toshiba, Kawasaki, Japan

[21] Appl. No.: 31,924

[22] Filed: Mar. 16, 1993

Related U.S. Application Data

[63] Continuation of Ser. No. 719,043, Jun. 21, 1991.

[30] Foreign Application Priority Data

| Jun. 25, 1990 | [JP] | Japan | 2-166412 |
| Mar. 26, 1991 | [JP] | Japan | 3-62100 |

[51] Int. Cl.$^6$ .................................................. G01N 21/88
[52] U.S. Cl. ............................................. 356/30; 356/237
[58] Field of Search ................................ 257/798; 356/30, 356/31, 237

[56] References Cited

U.S. PATENT DOCUMENTS

| 3,672,980 | 6/1972 | Glendinning et al. | 117/201 |
| 4,378,159 | 3/1983 | Galbraith | 356/237 |
| 4,391,524 | 7/1983 | Steigmeier et al. | 356/237 |
| 4,794,265 | 12/1988 | Quackenbos et al. | 356/237 |
| 4,902,131 | 2/1990 | Yamazaki et al. | 356/237 |
| 5,032,734 | 7/1991 | Orazio et al. | 250/572 |
| 5,076,692 | 12/1991 | Neukevmans et al. | 356/237 |
| 5,233,191 | 8/1993 | Noguchi et al. | 250/307 |

FOREIGN PATENT DOCUMENTS

| 63-122935 | 5/1988 | Japan. |
| 63-143831 | 6/1988 | Japan. |
| 63-298035 | 12/1988 | Japan. |
| 1-75943 | 3/1989 | Japan. |

OTHER PUBLICATIONS

Extended Abatracts (The 51st Autumn Meeting, 1990); The Japan Society of Applied Physics No. 2, 9. 681.
Dependence of 0.1 μm Particles on Sillicon Crystals, M. Miyashita et al. (1990 Sep. 26)
Locke et al. "Particle Sizing Uncertainties in laser Scanning of Silicon Wafers", *J. Electrochem. Soc.*, 134,7:1763–1771 (1987).
"A Comparative Study of Surface Particle Counters", *J. Electrochem. Soc.*, 136,10:3061–3070 (1989).
H. Mishima et al.—IEEE Transactions on Semiconductor Manufacturing, vol. 2, No. 3, pp. 69–75 Aug. 1989, "Particle–Free Wafer Cleaning and Drying Technology".

(List continued on next page.)

*Primary Examiner*—Richard A. Rosenberger
*Attorney, Agent, or Firm*—Foley & Lardner

[57] ABSTRACT

There are provided a method of inspecting and evaluating semiconductor substrates, good quality semiconductor substrates, a method of manufacturing good quality semiconductor substrates, and a method of manufacturing semiconductor devices using good quality semiconductor substrates.

A semiconductor substrate is processed with aqueous basic solution. In this process, the substrate is dipped in the aqueous solution or exposed to a vapor of the aqueous solution. With this process, the surface of the substrate is selectively etched. The substrate surface after the etching process is radiated with a laser beam to measure a light scattered point density. The quality of the substrate can be judged in accordance with the measured density. A thermal treatment may be carried out before or after processing the substrate with the aqueous basic solution. The thermal treatment considerably changes the fine defect density on the surface of the substrate. In accordance with such a change, the quality of the substrate may be judged. If a substrate judged as having a good quality is used, a semiconductor device having a good quality substrate can be obtained.

13 Claims, 8 Drawing Sheets

OTHER PUBLICATIONS

D. L. Tolliver et al.—Motorola Technical Developments. vol. 8, No. 1, pp. 3–4, Oct. 1988, "Means and Method for Cleaning Semiconductor Wafers".

Patent Abstracts of Japan, vol. 11, No. 23, Jan. 1987, & JP–A–61 193 456.

Dah–Bin Kao et al.—Extended Abstracts, vol. 88–1, May 15, 1988, Princeton, N.J., pp. 385–386, "The Effect of Chemical Cleaning of the Kinetics of Thermal Oxidation".

Patent Abstracts of Japan, vol. 10, No. 386, Dec. 24, 1986, & JP–A–61 176 125.

W. Kern,—Semiconductor International, vol. 7, No. 4, Apr. 1984, New York, pp. 94–99; "Purifying Si and SiO2 Surfaces with Hydrogen Peroxide".

IBM Technical Disclosure Bulletin., vol. 27, No. 10A, Mar. 1985, New York, pp. 5602–5603, "Improved Organic Clean for Removing Contaminants on Semiconductor Wafer Surfaces".

A. Ishizaka et al—Journal of the Electrochemical Society, vol. 133, No. 4, Apr. 1986, pp. 666–671, "Low Temperature Surface Cleaning of Silicon and Its Application to Silicon MBE".

Patent Abstracts of Japan, vol. 11, No. 127 (E–501) Apr. 21, 1987 & JP–A–61 270 829 (NEC).

Patent Abstracts of Japan, vol. 15, No. 304 (E–1906) Aug. 5, 1991 & JP–A–03 109 732, (Seiko Instr Inc.).

H. Ooi et al.—Extended Abstracts, vol. 90/2, Oct. 14, 1990, Princeton, N.J. pp. 444–445, "The Influence of Cleaning Method on Growth of Oxide Film on Si Wafers".

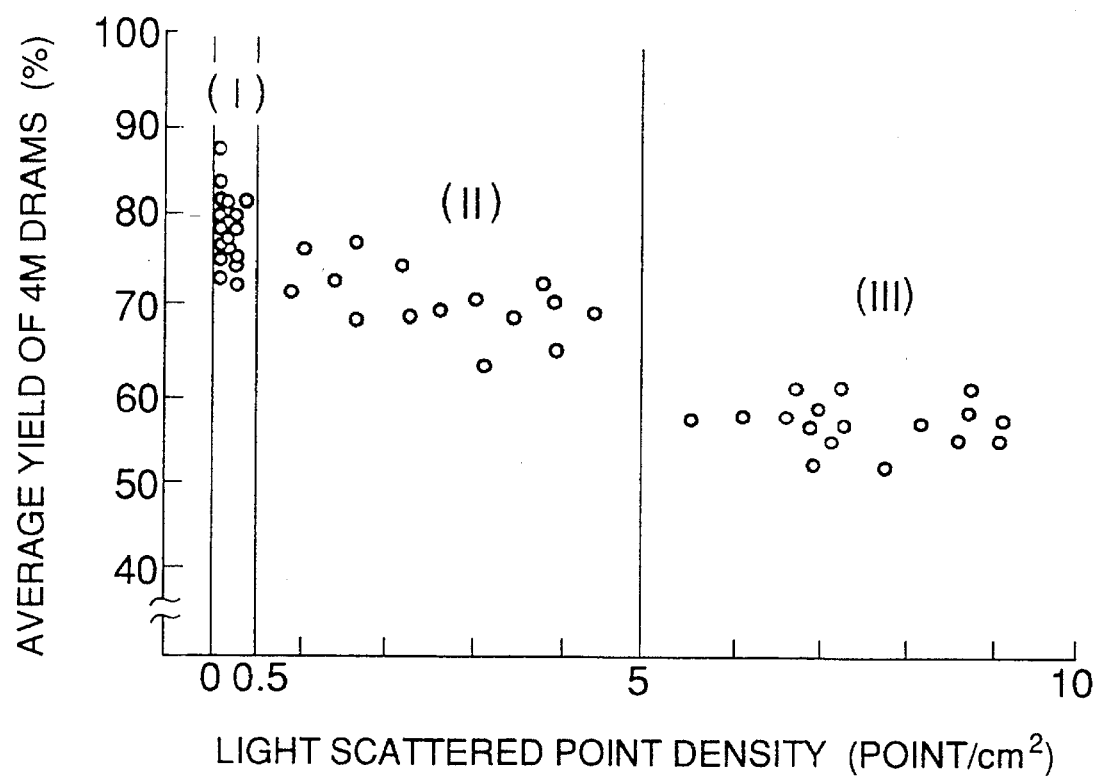
F I G . 6

COMPARISON OF DRAM YIELD BETWEEN PRESENT
INVENTION WAFERS AND CONVENTIONAL WAFERS

SEMICONDUCTOR SUBSTRATE, METHOD OF MANUFACTURING SEMICONDUCTOR SUBSTRATE AND SEMICONDUCTOR DEVICE, AND METHOD OF INSPECTING AND EVALUATING SEMICONDUCTOR SUBSTRATE

This application is a continuation, of application Ser. No. 07/719,043, filed Jun. 21, 1991.

FIELD OF THE INVENTION

The present invention relates to semiconductor substrates, a method of manufacturing semiconductor substrates and semiconductor devices, and a method of inspecting and evaluating semiconductor substrates.

BACKGROUND OF THE INVENTION

The quality of a silicon substrate used for manufacturing semiconductor devices greatly influences the yield and reliability of semiconductor devices. In view of this, various standards are prescribed to maintain the quality of a silicon substrate. Specifically, there are prescribed standards for resistivity, resistivity variation, interstitial oxygen concentration, oxidation-induced stacking fault (OSF), crystal orientation, size, planar degree, bowing, external appearance (nick, scratch, spike, haze, stain, etc.), and the like. Presently, there is only an OSF standard used as a standard for the crystal property of a region (device active region) near at the substrate surface on which a device is formed.

The integration density of a semiconductor device is becoming higher year after year. It is therefore difficult to maintain the yield and reliability of semiconductor devices by using only the above-described conventional standards. Particularly, in the case of the outer appearance standard for inspecting the substrate surface on which a device is formed, an expert person visually inspects using oblique rays. Such a conventional method provides an ability of detecting particles and unevenness only about 0.3 µm. Therefore, if a semiconductor substrate having passed such an inspection is used for manufacturing semiconductor devices by a design rule 0.8 µm or smaller, serious problems may often occur with respect to the yield and reliability.

Furthermore, as described above, in order to maintain the yield and reliability of semiconductor integrated circuit elements, it is necessary to make an Si substrate surface area or element active region completely non-defective. In addition, in order to deal with metallic contamination during the element manufacturing processes, it has become necessary to form crystal defects within a Si substrate under excellent controllability.

More in detail, a semiconductor device is formed on a silicon wafer surface by using various processes such as thermal treatment, etching, and film deposition. It is desirable that the structure of a wafer is preferably has no defect near at the wafer surface or element active region, and has an intrinsic gettering (IG) structure having bulk micro defects (BMD) for gettering metallic impurities. Therefore, the IG structure of a ULSI substrate is often formed by an in-process IG, i.e., by thermal treatments during processes including a high temperature process (up to 1200° C.), low temperature process (600° to 800° C.), and middle temperature process (up to 1000° C.). With this IG process, however, oxygen precipitation of low concentration is often present even in the non-defective layer at the Si substrate surface. Therefore, the electric characteristics are degraded by P-N junction leakage or the like of a semiconductor integrated circuit element.

The above-described visual inspection can detect only about 0.3 µm particles and surface defects on a substrate surface. If circuit elements are manufactured using a substrate having passed such a visual inspection, there has often occurred a problem of yield and reliability. It has been found by the present inventors that a fine defect of 0.1 µm or larger on a substrate surface takes an important roll in lowering the yield and the like.

As shown in FIG. 4, elements formed on a substrate having a fine defect density of 0.5 point/cm$^2$ or lower detected with a surface defect detecting apparatus showed a high yield.

However, the fine defect density of the surface of a generally used Si substrate is mostly 1/cm$^2$ or higher. It is difficult to obtain a high quality substrate having the fine defect density of 0.5 point/cm$^2$ or lower.

An epitaxial wafer is used in some cases to obtain a perfectly non-defective layer.

A description will be given below for a conventional method of evaluating an element active region as to whether or not it is really non-defective or not. First, a wafer is cleaved. A selective etching is carried out using a Wrigt etching method or a Secco etching method to expose BMDs which are then observed with a microscope. With this method, however, the size of observable defects has a limit. A BMD is considered that a nucleus originally present in a crystal grows by precipitation of oxygen around the nucleus during a thermal process. It is not clear that to what degree a BMD has grown can be observed by the above-described method. However, it is not possible to observe, for example, a nucleus itself or a BMD grown only to a small degree.

Recently, an infrared tomography method has been adopted to evaluate the distribution and number of BMDs by radiating an infrared ray (wavelength 1.06 µm or 1.32 µm) and measuring the infrared ray scattered by BMDs. However, an image is sometimes disturbed depending upon the configuration of a wafer surface. It is therefore impossible to measure small size BMDs.

As described above, it has been impossible heretofore to properly evaluate a semiconductor substrate. In addition, it is difficult to obtain a semiconductor substrate suitable for use in manufacturing highly integrated semiconductor devices, so that it is also difficult to obtain high quality semiconductor devices.

SUMMARY OF THE INVENTION

The present invention has been made in consideration of the above circumstances. It is an object of the present invention to provide a method of inspecting and evaluating semiconductor substrates, high quality semiconductor substrates, a method of manufacturing high quality semiconductor substrates, and a method of manufacturing semiconductor devices using manufactured high quality semiconductor substrates.

According to a first aspect of the present invention, there is provided a semiconductor substrate having at least one end surface thereof being finished as a mirror surface, the mirror surface being selectively etched by a process using aqueous basic solution.

According to a second aspect of the present invention, there is provided a method of inspecting a semiconductor substrate comprising the steps of:

preparing a semiconductor substrate having at least one end surface thereof being finished as a mirror surface, and selectively etching the mirror surface by a process using aqueous basic solution;

radiating a laser beam to the mirror surface of the substrate; and counting the number of laser beam scattered points on the mirror surface from which the laser beam was scattered, by using a detecting apparatus capable of detecting a scattered light from a particle having a diameter of at least 0.1 μm or larger.

According to a third aspect of the present invention, there is provided a method of evaluating a semiconductor substrate comprising:

a step of subjecting a semiconductor substrate to a thermal treatment;

a step of processing the substrate subjected to the thermal treatment, using aqueous basic solution; and a step of radiating a laser beam to the substrate processed by using the aqueous basic solution and measuring a density of laser beam scattered points on the surface of the substrate.

According to a fourth aspect of the present invention, there is provided a method of evaluating a semiconductor substrate comprising:

a step of measuring a density of first light scattered points on the surface of a semiconductor substrate still not processed, by using a laser beam;

a step of processing the semiconductor substrate using aqueous basic solution;

a step of subjecting the substrate processed by the aqueous solution to a thermal treatment;

a step of measuring a density of second light scattered points on the surface of the substrate processed and subjected to the thermal treatment, by using the laser beam; and a step of evaluating the substrate in accordance with the relationship between the densities of the first and second light scattered points.

According to a fifth aspect of the present invention, there is provided a method of manufacturing a semiconductor substrate comprising:

a step of processing a semiconductor substrate using aqueous basic solution;

a step of selecting a semiconductor substrate from the processed substrate, the selected substrate having a density equal to or lower than 0.5 to 20 points/cm$^2$ of defects having a size equal to or larger than 0.1 μm on the surface of the selected substrate; and a step of growing an epitaxial layer on the selected substrate.

According to a sixth aspect of the present invention, there is provided a semiconductor substrate processed using aqueous basic solution, the substrate having a density equal to or lower than 0.5 to 20 points/cm$^2$ of defects having a size 0.1 μm or larger, and having an epitaxial layer grown on the surface of the substrate.

According to a seventh aspect of the present invention, there is provided a method of manufacturing a semiconductor device comprising:

a step of etching a semiconductor substrate by 5 to 200 angstroms using alkaline solution;

a step of selecting a substrate from the etched substrate, the selected substrate having a density of 0.01 to 10 points/cm$^2$ of defects each having a size of 0.1 to 0.2 μm; and a step of using the selected substrate for forming various types of devices on the selected substrate, the step including a thermal treatment process at 1100° C. or higher for 3 hours.

BRIEF DESCRIPTION OF THE DRAWINGS

FIG. 6 is a graph showing the average yield of 4M DRAMs relative to a density of light scattered points.

DESCRIPTION OF THE PREFERRED EMBODIMENTS

In order to help understand the embodiments easily, the particulars how the present invention has been made will be described first, and then the embodiments will be described.

It is known that particles (foreign substances) on a mirror surface of a semiconductor substrate scatter a laser beam. However, the present inventors have found that a laser beam is scattered at the mirror surface of a semiconductor substrate subjected to the above-described manufacturing processes, not by particles (foreign substances) but by unevenness of a crystal defect portion on the layer of the mirror surface of the semiconductor substrate subjected to the above-described processes and selectively etched. The particulars of this finding will be described below.

Figure 3:
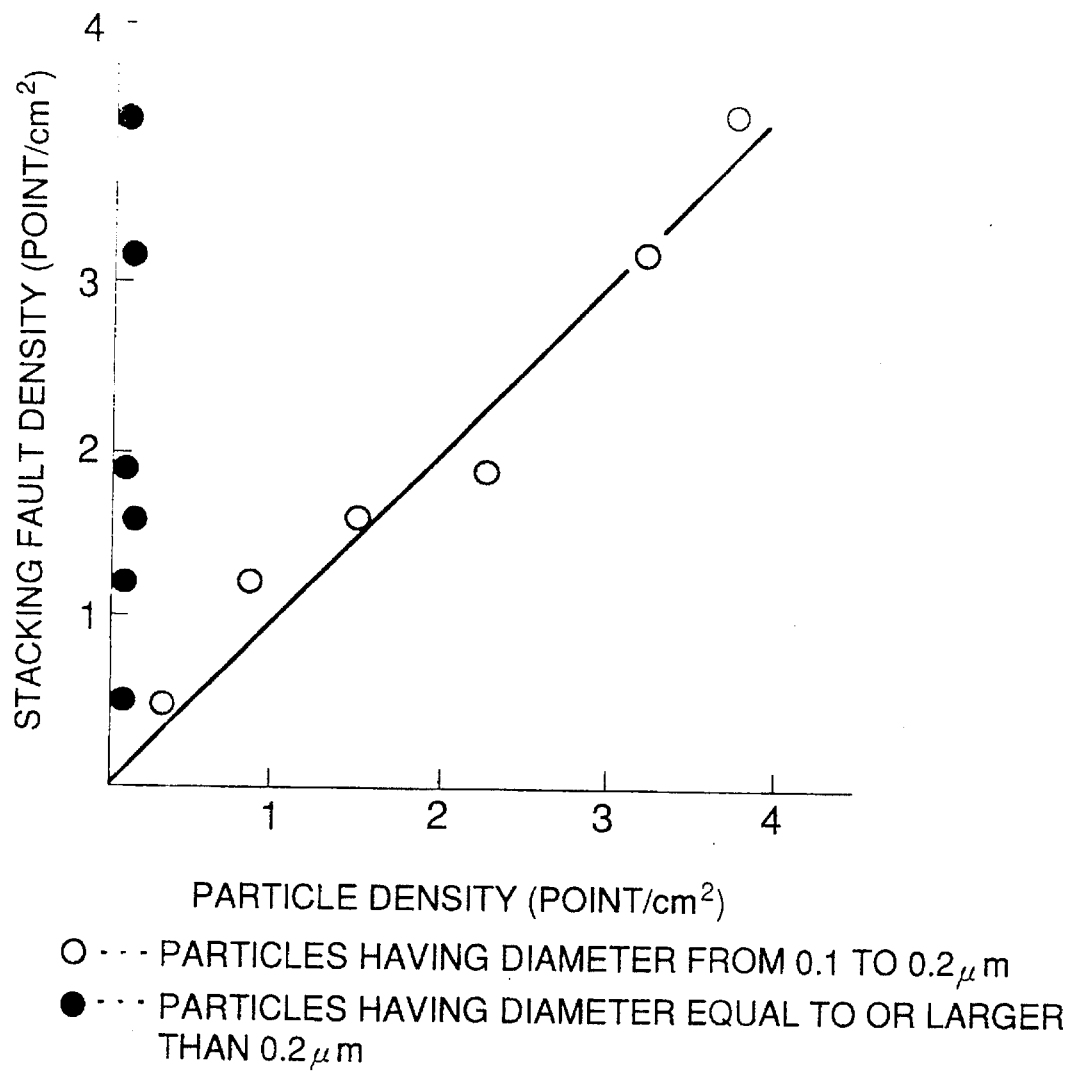
FIG. 3 is a graph showing crystal defects detected by the inspecting method according to the present invention.

Various semiconductor substrates are dipped in aqueous basic solution, and thereafter a laser beam is radiated to the mirror surface of each semiconductor substrate. A scattered light at the mirror surface is detected with a detecting apparatus to count the number of light scattered points on the mirror surface. This apparatus can detect a scattered light from a particle having a diameter of at least 0.1 μm, and can count the number of particles while discriminating the diameter thereof, assuming that the particle scattering the laser beam is a sphere. After these processes, each semiconductor substrate is subject to a high temperature thermal process (1000° C., 15 hours, oxygen atmosphere). Thereafter, the oxide film on the semiconductor substrate is removed. Then, the semiconductor substrate is subject to a Wrigt etching for selectively etching stacking faults. As a result, the stacking fault portion formed during the high temperature thermal process is etched to form an unevenness which can be detected with an optical microscope having a magnification factor of 100. A correlation between a particle density and a stacking fault density obtained by the above-described method is shown in FIG. 3 wherein laser beam scattered point at various semiconductor substrates have been assumed as a sphere. As seen from FIG. 3, there is a very tight correlation between the particle density for particles having a diameter of 0.1 to 0.2 μm and the stacking fault density, but there is no correlation between particle density for particles having a diameter of 0.2 μm or larger and the stacking fault density.

From this experiment results, the inventors have obtained the following finding. Namely, after the mirror surface of a semiconductor substrate is dipped in aqueous basic solution, a laser beam is radiated to the mirror surface and the scattered light at the mirror surface is detected by the detecting apparatus which can detect a scattered light from a particle having a diameter of at least 0.1 μm. The counted light scattered points on the mirror surface are very fine stacking faults serving as nuclei which grow during the high temperature thermal process.

The present inventors have obtained the same finding by exposing the mirror surface of a semiconductor substrate to a vapor of aqueous basic solution, instead of dipping the mirror surface in aqueous basic solution.

As described above, after the mirror surface of a semiconductor substrate is dipped in aqueous basic solution or exposed to a vapor of aqueous basic solution, a laser beam is radiated to the mirror surface, and the scattered light at the mirror surface is detected by the detecting apparatus to count the number of light scattered points. It is possible therefore to evaluate the semiconductor substrate, based on the counted number of light scattered points. It is preferred a measurement using the laser beam is carried out under the condition that the density of particles of 0.3 μm is equal to or lower than 1000 particles/ft$^3$.

A first embodiment (semiconductor substrate inspecting method) according to the present invention will be described below.

A silicon single crystal ingot grown by the Czochralski method (CZ method) is used to obtain a P-type silicon single crystal substrate (semiconductor substrate). This substrate has one surface finished as a mirror surface, a diameter 150 mm, thickness 625 μm, surface orientation (100), and a resistivity 4.5 Ω·cm with doped boron. The semiconductor substrate is dipped in aqueous basic solution of an alkaline nature (preferably pH 8 or larger). The aqueous basic solution is a mixture of aqueous ammonia (ammonia contents 28 weight %), aqueous hydrogen peroxide (hydrogen peroxide contents 30 weight %), and super-pure water at a volume ratio of 1:1:5. The temperature of the solution is maintained 80°±3° C. A crystal defect portion on the mirror surface dipped in the aqueous solution is selectively etched so that the defect portion on the mirror surface appears as unevenness. Thereafter, the substrate is washed with super-pure water for about 20 minutes. The washed substrate is dried by a rinser dryer which repels water contents by a centrifugal force.

The mirror surface of the semiconductor substrate subjected to the above processes is inspected using an argon ion laser having a wavelength of 488 nm. Specifically, the number of laser light scattered points on the substrate mirror surface is counted by a wafer surface defect detecting apparatus which uses the argon ion laser and can detect a defect having a diameter at least about 0.1 μm. The detecting apparatus is calibrated in advance using a standard sphere particle made of latex (merchandise name) and having a diameter of 0.1 μm. With this calibration, the detecting apparatus can detect a defect on the mirror surface having a diameter of about 0.1 μm. A semiconductor substrate determined from the count results as having 0.5 point/cm$^2$ laser beam scattered points or smaller is used as a substrate for manufacturing DRAMs under a design rule 0.8 μm.

Next, a second embodiment (semiconductor substrate inspecting method) will be described.

Figure 1:
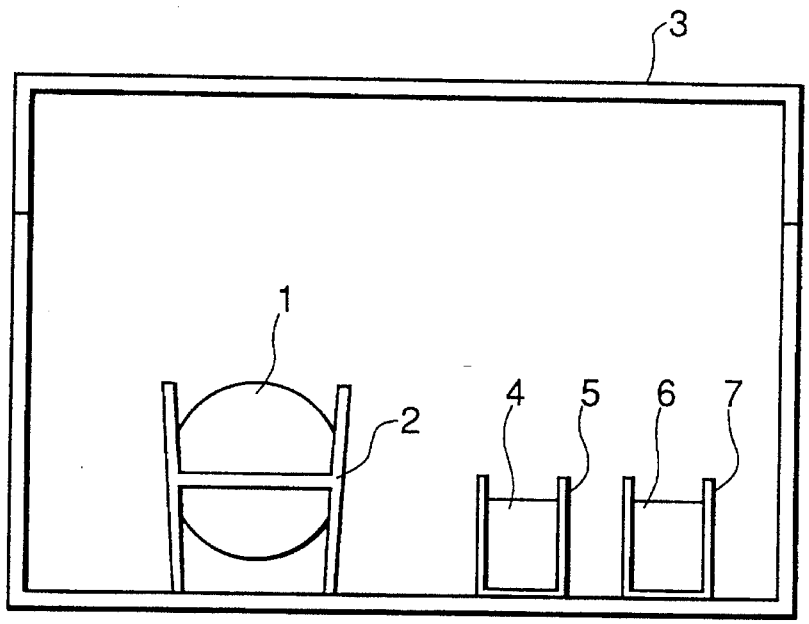
FIG. 1 is a cross sectional view showing an example of an apparatus used for practicing an inspecting method according to an embodiment of the present invention.

There is prepared an N-type silicon single crystal substrate (semiconductor substrate) obtained in the similar manner to the first embodiment. This substrate has one surface finished as a mirror surface, a diameter 150 mm, thickness 600 μm, surface orientation (100), and a resistivity 4.5 Ω·cm of the mirror surface with doped phosphorus. A silicon single crystal layer is grown by 25 μm on the mirror surface by means of epitaxial growth, and phosphorus is doped in the silicon single crystal layer to obtain a resistivity 35 Ω·cm. A substrate without the epitaxial grown layer may be used. As shown in FIG. 1, substrates 1, 1, . . . are supported by a supporting member 2 with a predetermined interval therebetween, the substrates being housed within a box 3 made of PTFE (polytetrafluoroethane, fluorine resin). A vessel 5 containing aqueous ammonia (ammonia contents 28 weight %) and a vessel 7 containing super-pure water 6 are additionally housed within the box 3. Thereafter, the box 3 is air-tightly sealed. With such an arrangement, the surface of the substrate 1 is exposed to ammonia vapor vaporized from the aqueous ammonia within the vessel 5. Similar to the case of the first embodiment, defects on the mirror surface is selectively etched. This condition is maintained for about 5 hours or longer. Thereafter, the substrate 1 is picked up from the box 3, washed with super-pure water for about 20 minutes, and dried with a rinser dryer. The above operation is carried out within a clean room controlled at a room temperature of 25°±1° C.

Thereafter, similar to the case of the first embodiment, the laser scattered points on the surface of the substrate 1 are counted by using a wafer surface defect detecting apparatus. A silicon single crystal substrate determined from the count results as having 0.5 point/cm$^2$ laser beam scattered points or smaller is used as a substrate for manufacturing CCD image pickup elements.

In the first and second embodiments, a semiconductor substrate is dipped in aqueous ammonia or exposed to ammonia vapor from aqueous ammonia. Instead of aqueous ammonia, basic aqueous solution, preferably pH 8 or larger, may be used. For example, as the basic aqueous solution, there may be used aqueous choline solution, aqueous potassium hydroxide solution, or aqueous sodium hydroxide solution. The aqueous choline solution is a mixture of aqueous choline (choline contents 4 weight %), aqueous hydrogen peroxide similar to that described above, and super-pure water at a volume ratio of 1:1:10. The aqueous potassium hydroxide is an aqueous solution having a pH about 9 obtained by resolving potassium hydroxide into water, and the aqueous sodium hydroxide solution is an aqueous solution having a pH about 9 obtained by resolving sodium hydroxide into water.

In the first and second embodiments, an argon ion laser having a wavelength of 488 nm is used. However, any other laser may be used if it can detect a defect having a diameter of about 0.1 μm. For example, an Ar⁺ laser having a wavelength of 496.5, 476.5, 472.7, 465.8, 457.9, or 454.5 nm or a Kr⁺ laser having a wavelength of 413.1, 468.0, 476.2 or 482.5 nm may also be used.

It is to be noted that a semiconductor substrate is dipped in aqueous ammonia or exposed to ammonia vapor so that not only a defect can be selectively etched as described above, but also a small stain on the semiconductor substrate surface can be removed, i.e. a so-called finishing process can be performed.

Figure 2:
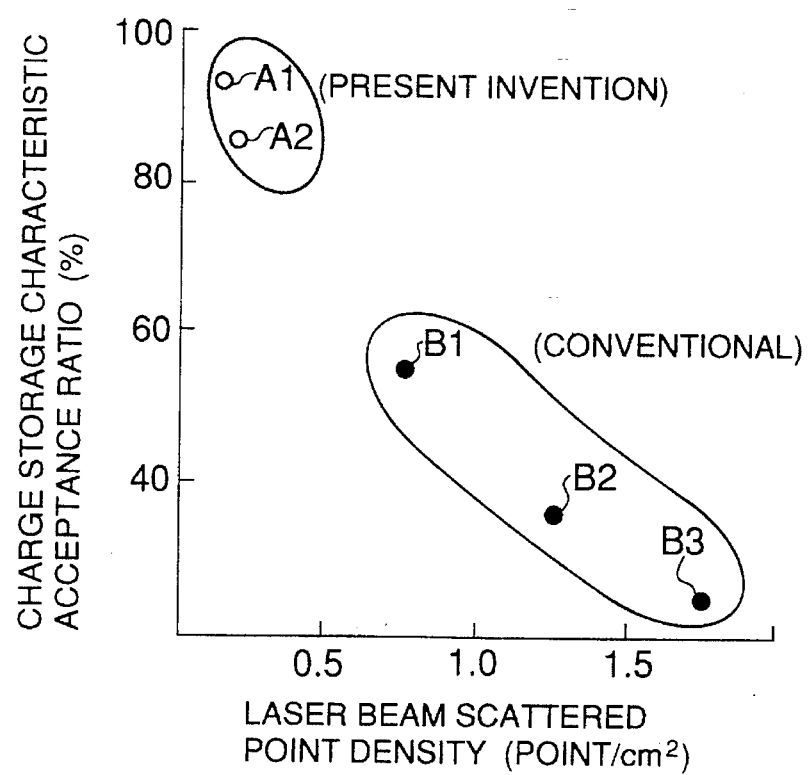
FIG. 2 is a graph comparatively showing the charge storage characteristics of DRAMs manufactured using semiconductor substrates selected according to the present invention, and of DRAMs manufactured using conventional semiconductor substrates.

DRAMs were manufactured using silicon substrates selected in the above embodiments as having a laser light scattered point density of 0.5 point/cm² or higher. Namely, using the silicon substrates, DRAMs A1 and A2 were manufactured according to a design rule 0.8 μm. The charge storage characteristic acceptance ratio of the capacitor of each DRAM is shown in FIG. 2. Similar DRAMs B1, B2, and B3 were manufactured using conventional silicon substrates having no particular standard. The charge storage characteristic acceptance ratio of the capacitor of each DRAM B1, B2, B3 is also shown in FIG. 2. As seen from FIG. 2, it has been found that the conventional substrates having no particular standard (light scattered point densities, about 0.75, 1.25, and 1.75) all showed an acceptance ratio of 60% or smaller, whereas the substrates (light scattered densities, about 0.25 and 0.13) selected according to the present invention showed a high acceptance ratio of 80% or larger. It is well known that the charge storage characteristics are greatly lowered by a presence of crystal defects. From the above experiment results, it can be understood that light scattered points are correlated with the crystal quality.

As described above, by manufacturing semiconductor devices using semiconductor substrates selected according to the present invention, the yield and reliability of semiconductor devices can be improved.

A third embodiment (inspecting method) according to the present invention will be described below.

A silicon single crystal ingot grown by the CZ method is used to obtain a P-type silicon single crystal substrate having a diameter 125 mm, thickness 625 μm, and surface orientation (100). One surface of the substrate is finished as a mirror surface. Boron is doped into the substrate to obtain a resistivity 4.5 Ω·cm. The Si semiconductor substrate is subject to a thermal treatment at 1100° C. for 2 hours under an oxygen and nitrogen atmosphere. Thereafter, the single crystal substrate is dipped in aqueous ammonium fluoride solution to peel off the surface oxide film. Thereafter, the single crystal substrate is dipped in an aqueous solution for 15 minutes. This aqueous solution is a mixture of aqueous ammonia (ammonia contents 28 weight %), aqueous hydrogen peroxide (hydrogen peroxide contents 30 weight %), and super-pure water at a volume ratio of 1:1:5. The temperature of the solution is maintained 80°±3° C. Thereafter, the silicon single crystal substrate is washed with super-pure water for 20 minutes, and dried with a rinser dryer. The number of laser light scattered points on the silicon wafer mirror surface is counted by a wafer surface defect detecting apparatus of a laser beam scatter type. The detecting apparatus is calibrated in advance using a standard sphere particle made of latex. With this calibration, the detecting apparatus can detect a sphere latex standard particle having a diameter of about 0.1 μm. The density of laser light scattered points is measured from the count results. It is possible to evaluate if a wafer is defective or acceptable in accordance with the measured density.

A fourth embodiment (inspecting method) according to the present invention will be described below.

A similar wafer (Si single crystal substrate) to the third embodiment is prepared. This wafer is subject to a thermal treatment at 750° C. for 3 hours under an oxygen atmosphere. Thereafter, a process is executed using aqueous basic solution similar to the third embodiment. Then, the wafer is washed and dried in the similar manner to the third embodiment. Thereafter, the density of light scattered points is measured using a wafer surface defect detecting apparatus of a laser beam scatter type similar to that described above. It is possible to evaluate if a wafer is defective or acceptable in accordance with the measured density.

Figure 5:
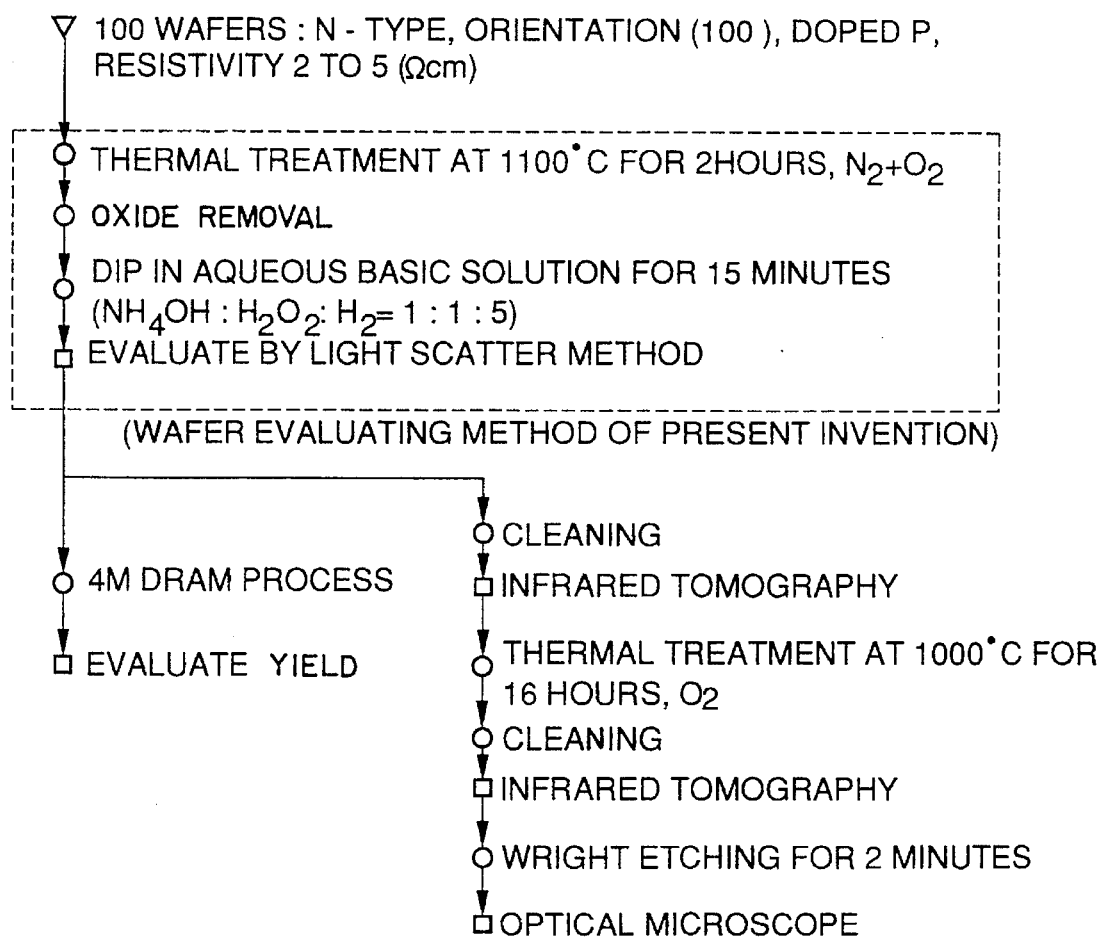
FIG. 5 is a flow chart illustrating the sequence of experimental processes.

4M DRAMs were manufactured using wafers evaluated in accordance with the third and fourth embodiments. In addition, the wafers were evaluated by conventional wafer evaluating methods ((1) a method of cleaving a wafer to expose its cross section, selectively etching it, and observing BMDs with an optical microscope. (2) an infrared tomography using BMD scattered infrared rays. The flow chart illustrating the experiment sequence is shown in FIG. 5.

There were prepared 100 N-type wafers having a surface orientation (100) and a resistivity 2 to 5 Ω·cm, and the wafers were evaluated in accordance with the third embodiment. 100 wafers were classified into three types in accordance with the densities of light scattered points having a size of 0.1 μm or larger.

| Type | Light Scattered Point Density For 0.1 μm or Larger | Number of Wafers |
|---|---|---|
| (I) | <0.5 | 36 |
| (II) | 0.5 to 5.0 | 30 |
| (III) | >5.0 | 34 |

These wafers were further classified into two groups. The first and second groups each include 18 wafers of the type (I), 15 wafers of the type (II), and 17 wafers of the type (III). The first group was used to manufacture 4M DRAMs, and the second group was evaluated in accordance with the above-described conventional evaluating methods.

There is shown in FIG. 6 a relationship between the D/S yield of 4M DRAMs manufactured using the first group wafers and the densities of light scattered points having a size of 0.1 μm or larger. It has been found from FIG. 6 that 4M DRAMs having a higher yield can be obtained by using wafers having a density equal to or lower than 0.5 point/cm² of light scattered points of 0.1 μm or larger evaluated in accordance with the third embodiment.

The evaluation results using the conventional evaluation methods were as follows.
(1) Selective Etching and Optical Microscope Observation A thermal treatment (1000° C., 16 hours, under O₂) was carried out to form BMDs for the observation of BMDs. Two regions were observed, one for observing an element active layer from the surface to the depth at 30 μm, and the other for observing the wafer interior from the depth at 200 μm to the depth at 400 μm. The observation results were as follows.

| | Depth from Surface | |
|---|---|---|
| | 0 to 30 μm (point/cm²) | 200 to 400 μm (point/cm²) |
| (I) | 0.1 | $3.7 \times 10^5$ |

-continued

| | Depth from Surface | |
|---|---|---|
| | 0 to 30 µm (point/cm$^2$) | 200 to 400 µm (point/cm$^2$) |
| (II) | 0.2 | 2.9 × 10$^5$ |
| (III) | 0.1 | 3.2 × 10$^5$ |

Each value in this Table is a mean value of BMDs at a central area of respective wafers of each type.

(2) Infrared Tomography

BMDs were observed by means of infrared tomography before and after BMD exposure thermal treatment. The observation region was from the surface to the depth at 30 µm same as the above region (1).

| | Before BMD Formation Thermal Treatment (point/cm$^2$) | After BMD Formation Thermal Treatment (point/cm$^2$) |
|---|---|---|
| (I) | 0.3 | 0.8 |
| (II) | 0.4 | 0.8 |
| (III) | 0.3 | 0.8 |

It has been found from the above observation results that the classification into types (I), (II), and (III) described in the above embodiment is impossible if the conventional evaluating methods are used. The scattering substances of 0.1 µm or larger evaluated in the above embodiment can be considered as BMD nuclei or nuclei grown to a small degree. Such scattering substances cannot be observed by the conventional evaluating methods.

Next, a fifth embodiment will be described.

An N-type silicon wafer having a diameter of 150 mm and grown by the CZ method is dipped in aqueous solution for 15 minutes. This aqueous solution is a mixture of aqueous ammonia (ammonia contents 28%), aqueous hydrogen peroxide (hydrogen peroxide contents 30%), and super-pure water at a volume ratio of 1:1:5. The temperature of the solution is maintained 80°±3° C. Thereafter, the wafer is washed with super-pure water for 20 minutes, and dried with a spin dryer. Next, the wafer is subject to a thermal treatment for one hour at 1100° C. and under an Ar 100% atmosphere. The wafer is inspected, i.e., the number of light scattered points on the wafer mirror surface is counted, before and after the thermal treatment, by using a wafer surface fine particle detecting apparatus of a laser beam scatter type using an argon laser having a wavelength of 488 nm. Wafers having a light scattered point density of 0.5 point/cm$^2$ are all selected. The selected wafers are classified into groups A, B and C. The group A includes wafers whose light scattered points reduced by ½ or more after the thermal treatment. The group B includes wafers conforming with a conventional standard. The group C includes wafers whose light scattered points did not reduce. Using wafers of groups A to C, DRAMs were manufactured under a design rule 0.8 µm or smaller to evaluate the electrical characteristics.

Figure 7:
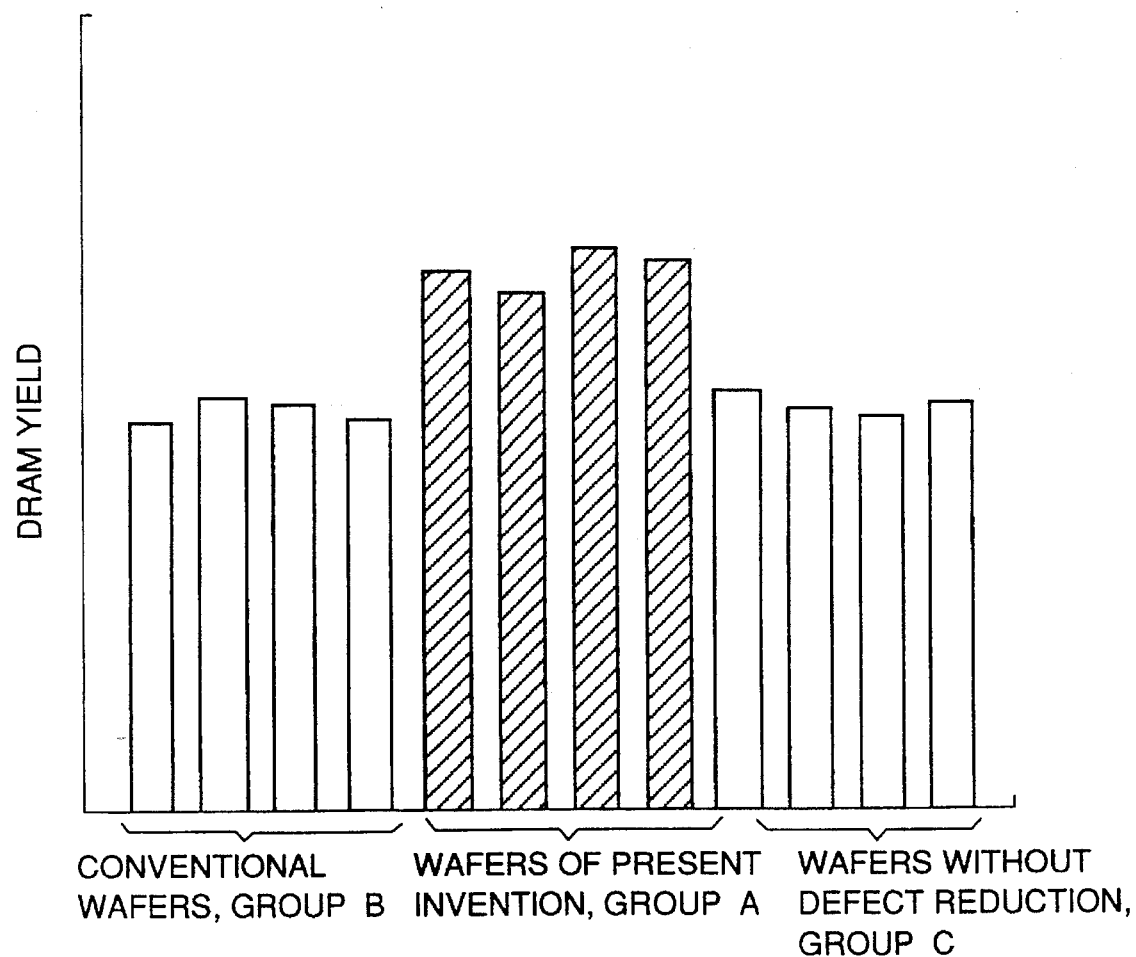
FIG. 7 is a graph showing the experiment results.

As shown in FIG. 7, there is no change at groups B and C. However, it was confirmed that wafers of group A had a yield improved by 10 to 20% as compared with that of group B wafers. The fraction defective of reliability of group A wafers was ½ or more of that of group B wafers, definitely confirming the advantages of the above embodiment.

A sixth embodiment will be described.

An N-type silicon wafer having a diameter of 150 mm and grown by the CZ method is dipped for 15 minutes in the aqueous solution same as that used in the fifth embodiment. The temperature of the solution is maintained 80°±3° C. Thereafter, the wafer is washed with super-pure water for 20 minutes, and dried with a spin dryer. Next, the wafer is subject to a thermal treatment for one hour at 1100° C. and under an Ar atmosphere. After the thermal treatment, light scattered points on the surface of the wafer are counted using an argon laser beam having a wavelength of 488 nm. Wafers having a light scattered point density of 0.5 point/cm$^2$ or lower before the thermal treatment are selected. Wafers among the selected wafers whose light scattered point density reduced ½ or lower are used for manufacturing 4M SRAMs. The yield was improved by about 10% as compared with wafers conforming with a conventional standard, and the pause acceptance ratio was improved by 50% or more. Wafers having a light scattered point density of 0.5 point/cm$^2$ before the thermal treatment are further selected. The selected wafers are used for manufacturing 4M SRAMs at the same lot. These 4M SRAMs have no significant difference from those conforming with a conventional standard.

It becomes possible to improve the yield and reliability of semiconductor devices by using semiconductor substrates selected in accordance with the fifth and sixth embodiments. Specifically, a conventional standard is only the OSF for inspecting the crystal property of a device active region near a wafer surface. The OSF poses no problem for those devices having a low integration density. However, in the case of devices manufactured under a design rule 0.8 µm or smaller, a presence of defects on the substrate surface which are detectable only by a laser scattered beam as described with the fifth embodiment will lower the yield. On the other hand, according to the fifth and sixth embodiments, it is possible to select semiconductor substrates having a good crystal property. By using substrates selected in such a manner, it is possible to obtain devices having a higher yield and higher reliability, even for DRAMs having a higher integration density (design rule 0.8 µm or smaller).

Next, seventh and eighth embodiments (substrate manufacturing method) will be described. The general description for the seventh and eighth embodiments will be first given below.

A semiconductor substrate having an oxide concentration of 9.5 to 12×10$^{17}$ atoms/cm$^2$ (converted to JEIDA) is used to obtain the intrinsic gettering (IG) effect during the device manufacturing processes. The semiconductor substrate is dipped in aqueous basic solution having a pH 8 or larger, or exposed to a vapor of the aqueous basic solution. After this processing, defects on the surface are detected using a method which allows to detect defects having a size of 0.1 µm or larger. A substrate having a fine defect density from 0.5 point/cm$^2$ or higher to 20 points/cm$^2$ or lower is selected, and an epitaxial layer is grown on the surface of the selected substrate. In this manner, a semiconductor substrate used for manufacturing devices is obtained.

The seventh embodiment will be described below.

There is prepared a P-type Si single crystal grown by the CZ method and having one surface finished as a mirror surface, a diameter 125 mm, thickness 625 µm, and surface orientation (100). The substrate is dipped in aqueous solution for 15 minutes at the solution temperature of 80° C. The aqueous solution is a mixture of aqueous ammonia (ammonia contents: 28%), aqueous hydrogen peroxide (hydrogen peroxide contents: 30%), and super-pure water at a volume ratio of 1:1:5. Thereafter, the Si substrate is washed with super-pure water for 20 minutes, and dried by a rinser dryer. The surface of the Si substrate subjected to the above processes is inspected using a wafer surface defect detecting apparatus of a laser beam scatter type using an $Ar^+$ laser beam having a wavelength of 488 nm, to thereby detect fine defects on the substrate surface. As the wafer surface defect detecting apparatus, there is used an apparatus capable of detecting a sphere latex particle having a diameter of 0.1 μm or larger. In accordance with the detection results of the surface defect detecting apparatus, there is selected a substrate having a fine defect density at the substrate surface from 0.5 point/cm$^2$ or higher to 20 points/cm$^2$ or lower. An epitaxial p-layer of 5 μm is grown on the surface of the selected substrate, using raw material gas $SiH_2Cl_2$, carrier gas $H_2$, and dopant $B_2H_6$.

The eighth embodiment is a modification of the seventh embodiment. There is prepared a substrate having an oxygen concentration of 9.5 to $12 \times 10^{17}$ atoms/cm$^3$ (converted to JEIDA). This substrate is subject to the processes same as described with the seventh embodiment.

A comparative example will be described which is used for confirming the advantageous effect of the seventh and eighth embodiments. A substrate having a fine defect density equal to or higher than 20 points/cm$^2$ obtained by the defect detecting apparatus of the seventh embodiment is subject to a vapor growth in the similar manner to the seventh embodiment.

The planar degrees of the epitaxial wafer surfaces obtained by the seventh and eighth embodiments were good. The fine defects on the substrate surface after a process using aqueous ammonia/aqueous hydrogen peroxide/super-pure water was 0.5 point/cm$^2$ or smaller for both the seventh and eighth embodiments. Namely, the surfaces of high quality were obtained. In contrast with this, the epitaxial wafer substrate surface of the comparative example was rough and had unevenness, so that a substrate surface suitable for manufacturing device elements was not obtained.

As described above, according to the seventh and eighth embodiments, substrates having a high quality surface equal to or lower than 0.5 point/cm$^2$ were obtained from substrates having a fine defect density of about 1 to 20 points/cm$^2$ generally used in this field of technology.

Figure 4:
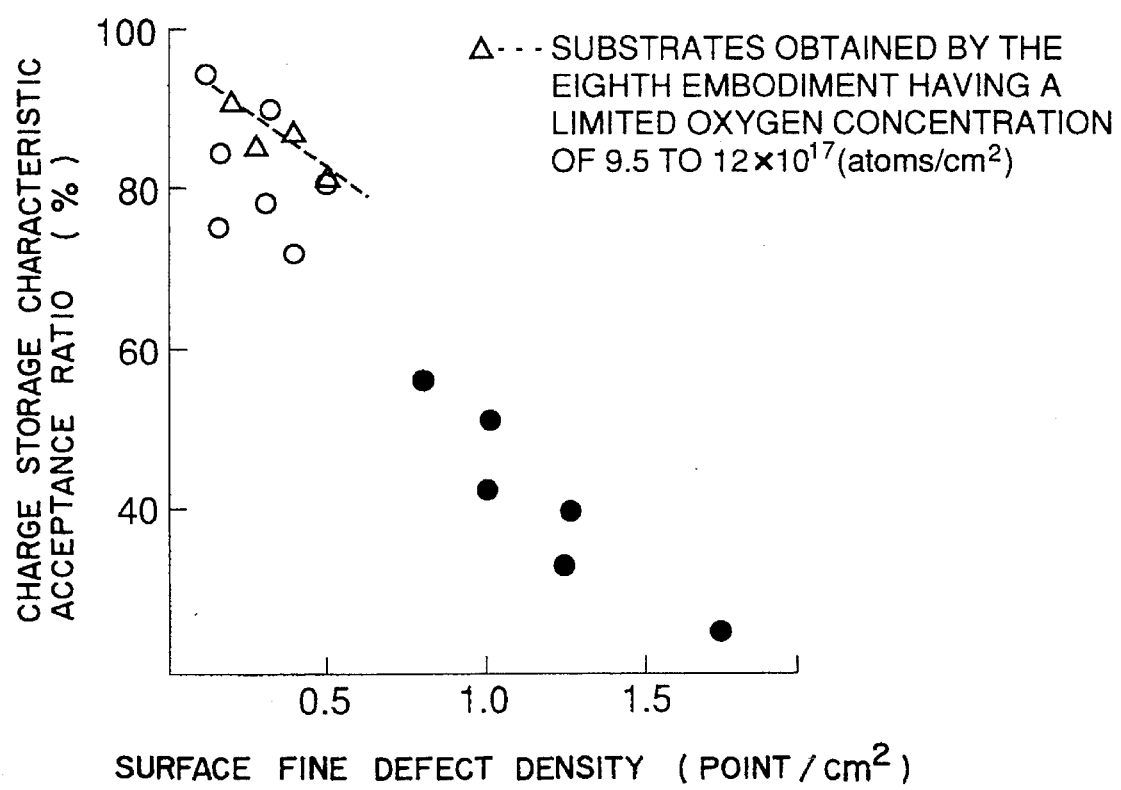
FIG. 4 is a graph showing the characteristics of a dependency of a charge storage characteristic acceptance ratio upon a substrate surface fine defect.

Device elements were manufactured using a substrate having a surface fine defect density equal to or lower than 2 points/cm$^2$. The electrical characteristics such as charge storage characteristic and the like of the device elements were inspected. As seen from FIG. 4, a high acceptance ratio was obtained for substrates having a defect density equal to or lower than 0.5 point/cm$^2$. Particularly, a substrate obtained by the eighth embodiment had a small variation of acceptance ratio and always showed a high acceptance ratio (indicated by triangles in FIG. 4). The reason for this is that influence of impurity contamination was suppressed to a low degree by the IG effect during the element manufacturing processes.

As described above, a high yield with respect to electrical characteristics and the like can be obtained from a combination of a high quality substrate surface having a defect density equal to or lower than 0.5 point/cm$^2$ and the IG capability.

As described with the seventh and eighth embodiments, a semiconductor substrate is dipped in aqueous basic solution or exposed to a vapor of the solution, and fine defects on the processed surface are inspected. In this way, it becomes possible to easily obtain a high quality substrate having a fine defect density equal to or lower than 0.5 point/cm$^2$. A semiconductor substrate generally used has a fine defect density equal to or higher than 1 point/cm$^2$.

By using a high quality substrate having a defect density equal to or lower than 0.5 point/cm$^2$ and the IG capability, the acceptance ratio of electrical characteristics and the like of manufactured semiconductor devices can be improved considerably. Namely, the yield and reliability can be improved considerably as compared with those of conventional substrates.

Next, a ninth embodiment (semiconductor device manufacturing method) will be described.

Figure 8:
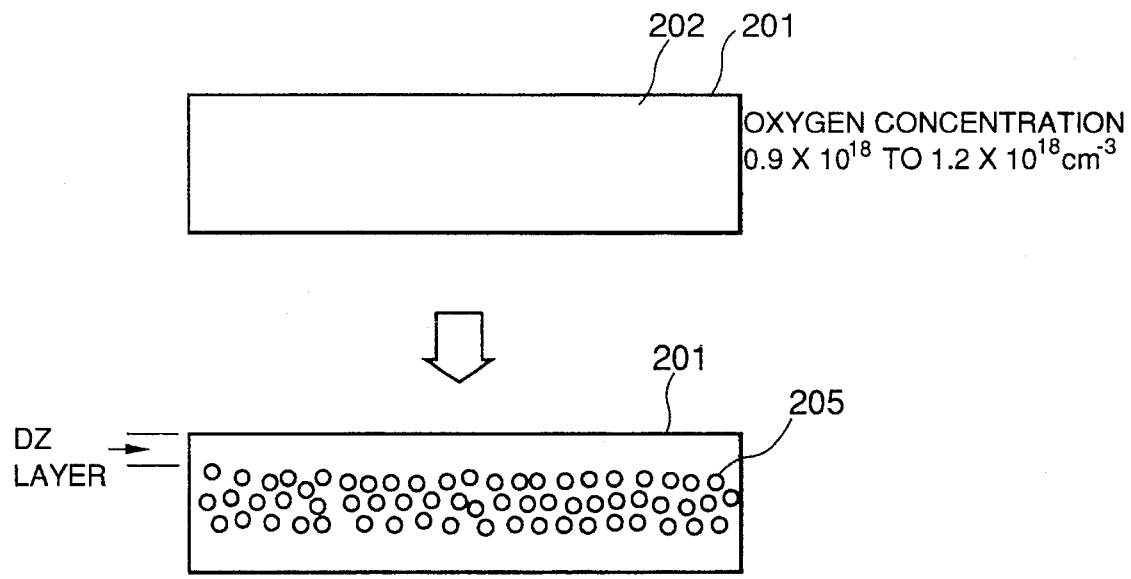
FIG. 8 is cross sectional views showing a semiconductor substrate after and before the semiconductor device manufacturing processes.

This embodiment is provided according to the following finding by the present inventors. Specifically, a Si substrate having a density 0.01 to 10 points/cm$^2$ of fine defects of 0.1 to 0.2 μm is subject to a thermal treatment at 1100° C. for 3 hours or longer. Thereafter, oxygen precipitation substances are formed within the substrate. It has been found that in this case the oxygen precipitation density at the substrate surface can be made zero. The following embodiment utilizes this phenomenon. As shown in FIG. 8, the density of fine defects of 0.1 to 0.2 μm at the surface of a Si substrate 201 used for manufacturing semiconductor devices is set to 0.01 to 10 points/cm$^2$. During the device element manufacturing processes, a thermal treatment is carried out at 1100° C. for 3 hours or longer. As a result, the oxygen precipitation density of the element active layer on the Si substrate surface becomes 0 point/cm$^2$. In order to observe fine defects of 0.1 to 0.2 μm on the Si substrate surface, it is preferable to etch the Si substrate by 5 to 200 angstroms using alkaline solution. As the alkaline solution etching, a wash process for washing Si with alkaline solution may be used. It is a characteristic point of this embodiment that fine defects on the substrate surface can be vanished by the thermal treatment at 1100° C. for 3 hours or longer during the element manufacturing processes. If the fine defect density is equal to or higher than 10 points/cm$^2$, it is difficult to sufficiently vanish fine defects on the Si substrate surface even by the thermal treatment at 1100° C. for 3 hours or longer. Therefore, the fine defect density should be equal to or lower than 10 points/cm$^2$.

The following facts are already known. Namely, if a Si substrate having an oxygen concentration equal to or higher than $9 \times 10^{18}$ cm$^{-3}$ is used, it is possible to form fine defects (oxygen precipitation) 205 within the Si substrate by the thermal treatment process during the semiconductor device manufacturing processes. However, if a Si substrate having an oxygen concentration equal to or lower than 0.01 point/cm$^2$ is used, it is difficult to form oxygen precipitation within the substrate. Accordingly, the fine defect density at the Si substrate surface should be equal to or higher than 0.01 point/cm$^2$. It is not necessary to define a particular atmosphere for the thermal treatment at 1100° C. for 3 hours or longer. This thermal treatment process may be carried out at the same time when a high temperature process such as a well diffusion process or the like is carried out, if temperature and time conditions are satisfied.

With a substrate oxygen concentration equal to or lower than $0.9 \times 10^{18}$ cm$^{-3}$ it is not possible to sufficiently form fine defects within the Si substrate by the thermal treatment process during the manufacturing processes. On the contrary, with a substrate oxygen concentration equal to or higher than $12 \times 10^{18}$ cm$^{-3}$, it is not possible to vanish fine defects on the substrate surface because of too high an oxygen concentration. Accordingly, the oxygen concentration within the substrate should be set to $0.9 \times 10^{18}$ cm$^{-3}$ to $1.2 \times 10^{18}$ cm$^{-3}$.

The embodiment will be described while comparing it with two conventional example.

EMBODIMENT

An CzSi wafer (resistivity 4 to 6 Ω·cm, oxygen concentration $1.0 \times 10^{18}$ cm$^{-3}$) with doped B and surface orientation (100) is etched by 100 angstroms using an alkaline etching solution ($NH_4OH:H_2O_2:H_2O=1:1:5$ (weight ratio)). Thereafter, there is selected an Si wafer whose density of surface fine defects of 0.1 to 0.2 μm is $5/cm^2$. Using the selected wafer, 4M DRAMs of peripheral CMOS structure were manufactured. A well thermal treatment process was carried out at 1150° C. for 5 hours.

CONVENTIONAL EXAMPLE 1

Without evaluating surface fine defects, 4M DRAMs were manufactured using an Si wafer in the similar manner to the above embodiment.

CONVENTIONAL EXAMPLE 2

Without evaluating surface fine defects, an Si wafer was subjected to the IG thermal treatment (at 1175° C. for 5 hours, and then at 750° C. for 20 hours).

Figure 10:
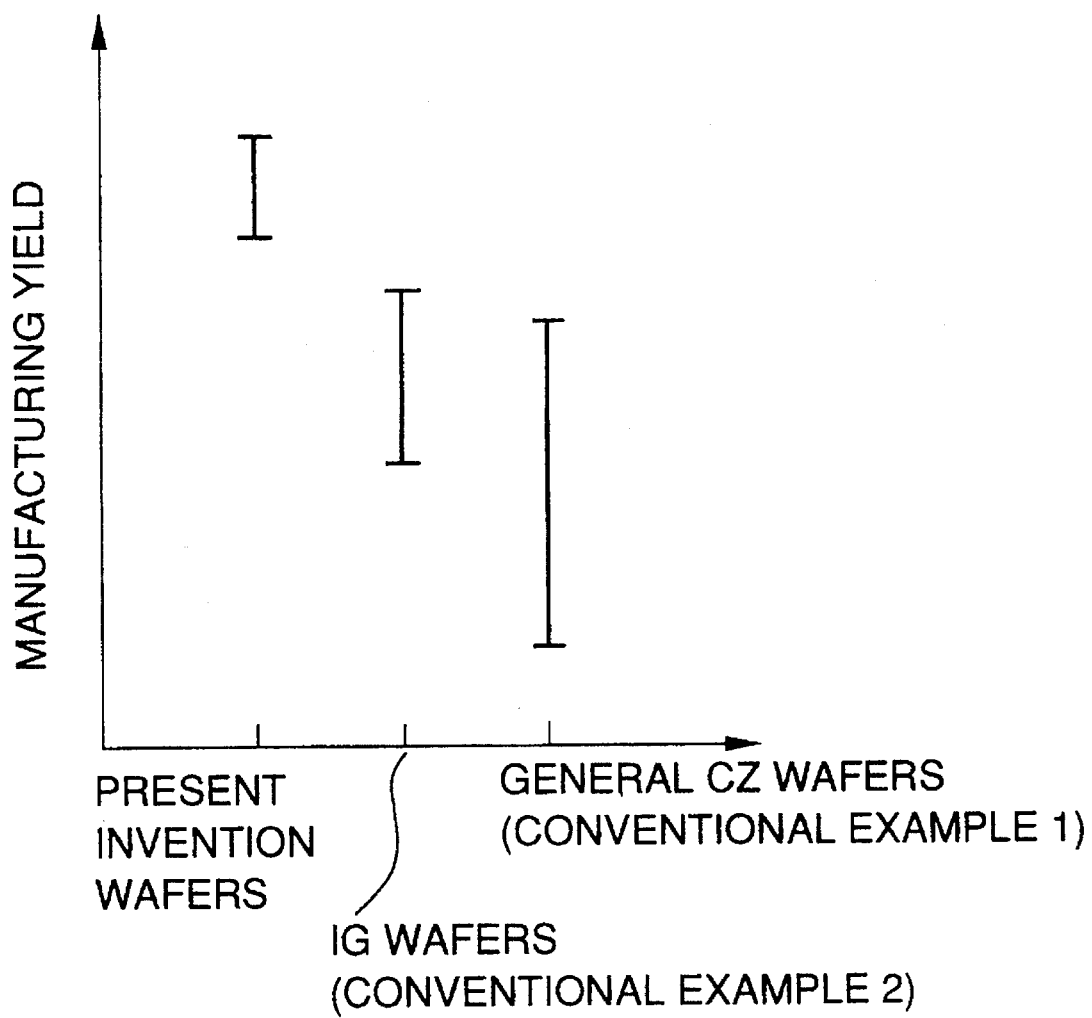
FIG. 10 is a graph comparatively showing the manufacturing yield of DRAMs of the embodiment and that of conventional DRAMs.

The above embodiment is one of the embodiments of the present invention. The conventional example 1 is a general conventional example. The conventional example 2 is an example using the IG method. The manufacturing yield of 4M DRAMs was checked. As shown in FIG. 10, the manufacturing yields were conventional example 1>conventional example 2>embodiment 1. The deviations of yields were conventional example 1> conventional example 2> embodiment 1. It was found that both the yield and deviation of the embodiment were superior to those of the conventional example 1 and 2.

Figure 9:
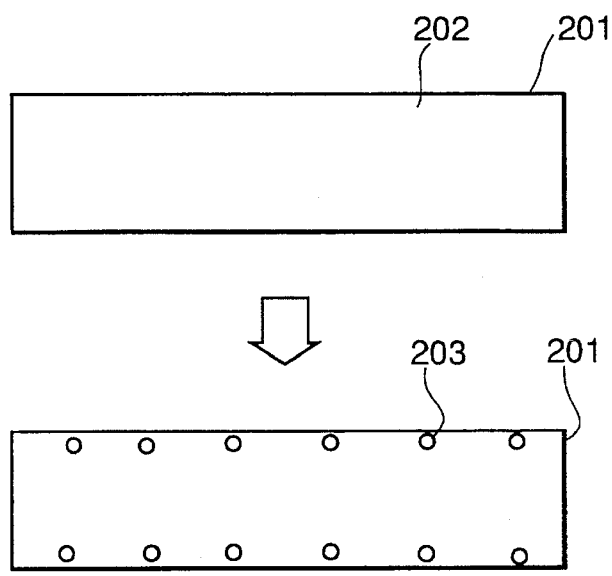
FIG. 9 is cross sectional views showing a semiconductor device after and before conventional semiconductor device manufacturing processes.

The checked crystal defect densities of manufactured 4M DRAMs were embodiment (0 point/$cm^2$)<conventional example 2<conventional example 1. The fine defect densities within the wafers were embodiment - conventional example 2> conventional example 1 - 0 point/$cm^2$. It can be considered from the above results that as shown in FIG. 9 the conventional example 1 has a high density of surface defects 203 resulting in a low manufacturing yield, and that the conventional example 1 has almost no fine defects within the substrate resulting in no gettering effect and a large yield deviation. As shown in FIG. 10, the conventional example 2 has a smaller yield deviation than that of the conventional example 1 because of internal fine defects, and also has an improved yield. However, it can be considered that fine defects at the substrate surface were not sufficiently vanished at the IG thermal treatment process and so the remaining fine defects at the substrate surface made the manufacturing yield and deviation inferior to those of the embodiment. As shown in FIG. 8, according to the embodiment, fine defects are formed within the substrate at the thermal treatment during the manufacturing processes because of the above-described effects, and in addition, fine defects at the substrate surface were made substantially zero because of the well process.

In the above embodiment, as the alkaline solution, $NH_4OH+H_2O_2$ is used by way of example. Another alkaline solution may be used if it has a pH 7 or larger. With an etched depth equal to or smaller than 5 angstroms, it is difficult to detect fine defects. With an etched depth equal to or larger than 200 angstroms, it is also difficult to detect fine defects because the surface is damaged. In the above embodiment, the surface fine defect density of 5 points/$cm^2$ is used by way of example. However, even with the density of 0.01 to 10 points/$cm^2$, the similar effects of the embodiment can be obtained for the reasons described previously. Furthermore, in the above embodiment, the thermal treatment during the device manufacturing processes is carried out at 1150° C. for 5 hours. The similar effects for the thermal treatment can be expected by a thermal treatment at 1100° C. or higher and for 3 hours or longer. Under the conditions other than those described above, surface fine defects become hard to be vanished, posing a problem in practical use. In the above embodiment, a P-type wafer 100 grown by CZ method is used by way of example. The effects of the present invention do not depend on the crystal growing method, conductivity type, surface orientation, and resistivity.

One of the characteristics of the embodiment is that the etching depth of the substrate surface by alkaline solution is set to an extremely shallow depth of 5 to 200 angstroms. Therefore, if there is no problem of contamination, wafers whose fine defects have been checked can be used for manufacturing semiconductor devices.

In the above embodiment, 4M DRAMs are used by way of example. It has been confirmed that the similar effects of the embodiment can be obtained for semiconductor devices such as MOS devices, bipolar devices, and BiCMOS devices.

According to the ninth embodiment, it is possible to reduce crystal-related defects of a semiconductor device by using a very simple method, and to improve the manufacturing yield of semiconductor devices. It is also possible to prevent the manufacturing yield from being lowered by process-related causes such as process contamination. For example, it has been confirmed that the yield of 4M DRAMs manufactured by the embodiment is improved by 10 to 15%.

What is claimed is:

1. A method of inspecting a semiconductor substrate comprising the steps of:

selectively etching a mirror surface formed on at least one surface of a semiconductor substrate by a process using aqueous basic solution;

radiating a laser beam upon the mirror surface of the semiconductor substrate; and determining the number of defects by counting light scattered points that correspond to particles with diameters from 0.1 to 0.2 μm.

2. The method of claim 1, wherein the step of selectively etching the mirror surface of the semiconductor substrate comprises a step of dipping the semiconductor substrate into the aqueous basic solution.

3. The method of claim 2, which further comprises a step of determining whether the density of the laser beam scatter points obtained by the counting process is less than 0.5 point/$cm^2$ at an arbitrary area.

4. The method of claim 1, wherein the defects are stacking fault defects.

5. A method of evaluating a semiconductor substrate, comprising the steps of:

radiating a laser beam upon a surface of an unprocessed semiconductor substrate;

counting the number of light scattered points that correspond to particles with diameters from 0.1 to 0.2 μm to give a first scatter point density;

processing the semiconductor substrate with an aqueous basic solution;

heat treating the semiconductor substrate processed by the aqueous basic solution;

radiating a laser beam upon the surface of the heat treated semiconductor substrate;

counting the number of light scattered points that correspond to particles with diameters from 0.1 to 0.2 μm on the surface of the heat treated semiconductor substrate to give a second scatter point density; and selecting the semiconductor substrate for further device processing if the second scatter point density is less than half of the first density point density.

6. The method of claim 5, wherein the step of processing the semiconductor substrate with the aqueous basic solution is a step of dipping the semiconductor substrate into the aqueous solution.

7. The method of claim 6, wherein the step of heat treating is carried out at 1100° C. or higher in an inert gas atmosphere.

8. The method of claim 7, wherein the first scatter point density less than 0.5 point/cm$^2$.

9. The method of claim 6, wherein the first scatter point density less than 0.5 point/cm$^2$.

10. The method of claim 5, wherein the step of heat treating is carried out at 1100° C. or higher in an inert gas atmosphere.

11. The method of claim 10, wherein the first scatter point density less than 0.5 point/cm$^2$.

12. The method of claim 5, wherein the first scatter point density less than 0.5 point/cm$^2$.

13. The method of claim 5, wherein the defects are stacking fault defects.

* * * * *